United States Patent
Wilder Smith et al.

(10) Patent No.: US 12,161,288 B2
(45) Date of Patent: Dec. 10, 2024

(54) ORAL AND OROPHARYNGEAL CANCER SCREENING SYSTEM AND METHODS OF USE

(71) Applicants: The Regents of the University of California, Oakland, CA (US); Arizona Board of Regents on Behalf of the University of Arizona, Tucson, AZ (US)

(72) Inventors: Petra Beate Wilder Smith, San Juan Capistrano, CA (US); Rongguang Liang, Tucson, AZ (US)

(73) Assignees: The Regents of the University of California, Oakland, CA (US); Arizona Board of Regents on Behalf of the University of Arizona, Tucson, AZ (US)

( * ) Notice: Subject to any disclaimer, the term of this patent is extended or adjusted under 35 U.S.C. 154(b) by 542 days.

(21) Appl. No.: 17/258,989

(22) PCT Filed: Jul. 22, 2019

(86) PCT No.: PCT/US2019/042811
§ 371 (c)(1),
(2) Date: Jan. 8, 2021

(87) PCT Pub. No.: WO2020/023377
PCT Pub. Date: Jan. 30, 2020

(65) Prior Publication Data
US 2021/0307597 A1    Oct. 7, 2021

Related U.S. Application Data

(60) Provisional application No. 62/702,184, filed on Jul. 23, 2018.

(51) Int. Cl.
*A61B 1/00* (2006.01)
*A61B 1/005* (2006.01)
(Continued)

(52) U.S. Cl.
CPC .. *A61B 1/000095* (2022.02); *A61B 1/000096* (2022.02); *A61B 1/0051* (2013.01);
(Continued)

(58) Field of Classification Search
CPC . A61B 1/000096; A61B 1/0051; A61B 1/043; A61B 1/05; A61B 1/0676;
(Continued)

(56) References Cited

U.S. PATENT DOCUMENTS 5,638,823 A * 6/1997 Akay .................. A61B 5/7264
600/501
5,647,368 A * 7/1997 Zeng ................... A61B 5/4255
600/476

(Continued)

FOREIGN PATENT DOCUMENTS

EP    3777644 A1 * 2/2021    ......... A61B 1/00009

OTHER PUBLICATIONS

International Search Report and Written Opinion, PCT/US2019/042811, mailed Oct. 3, 2019.

*Primary Examiner* — Anh Tuan T Nguyen
*Assistant Examiner* — Shankar Raj Ghimire
(74) *Attorney, Agent, or Firm* — Master Key IP, LLP; Justin G. Sanders (57) ABSTRACT

An oral and oropharyngeal cancer screening system and associated methods are disclosed. In at least one embodiment, the screening system provides an at least one oral and oropharyngeal cancer screening device configured for selectively capturing images of an oropharyngeal area of an at least one patient. The screening device provides an elongate, (Continued)

relatively compact housing, a distal end of the housing being selectively bendable. An imaging module is positioned within the housing, the imaging module providing a lens, an at least one light source, and an imaging sensor positioned in the distal end of the housing. A user application resides in memory on an at least one user device in selective communication with the at least one screening device. The user application is configured for receiving images captured by the at least one screening device and recording risk factors, automatically analyzing the captured images and potential health-risk factors to screen for OPML and oral and oropharyngeal risk.

16 Claims, 6 Drawing Sheets

(51) Int. Cl.
- *A61B 1/04* (2006.01)
- *A61B 1/05* (2006.01)
- *A61B 1/06* (2006.01)
- *A61B 1/24* (2006.01)
- *A61B 5/00* (2006.01)

(52) U.S. Cl.
CPC ............... *A61B 1/043* (2013.01); *A61B 1/05* (2013.01); *A61B 1/0676* (2013.01); *A61B 1/24* (2013.01); *A61B 5/7264* (2013.01); *A61B 5/7275* (2013.01)

(58) Field of Classification Search
CPC ....... A61B 1/24; A61B 5/7264; A61B 5/7275; A61B 1/0055
See application file for complete search history.

(56) References Cited

U.S. PATENT DOCUMENTS

| | | | | |
|---|---|---|---|---|
| 5,800,342 | A * | 9/1998 | Lee | A61B 1/32 600/114 |
| 8,629,919 | B2 * | 1/2014 | Imai | H04N 23/88 382/167 |
| 8,993,333 | B2 * | 3/2015 | Chaubron | G01N 33/57407 436/63 |
| 2003/0135122 | A1 * | 7/2003 | Bambot | A61B 5/4312 600/476 |
| 2003/0184660 | A1 * | 10/2003 | Skow | H04N 23/88 348/223.1 |
| 2004/0006276 | A1 | 1/2004 | Demos et al. | |
| 2004/0010197 | A1 * | 1/2004 | Faupel | A61B 5/0075 600/476 |
| 2004/0245350 | A1 * | 12/2004 | Zeng | A61B 1/042 236/77 |
| 2005/0059894 | A1 * | 3/2005 | Zeng | A61B 5/0075 600/476 |
| 2007/0015963 | A1 * | 1/2007 | Fengler | A61B 1/043 348/E5.029 |
| 2009/0270678 | A1 * | 10/2009 | Scott | A61B 1/000096 600/109 |
| 2010/0049078 | A1 * | 2/2010 | Faupel | A61B 5/24 600/547 |
| 2010/0210023 | A1 * | 8/2010 | Wong | G01N 33/57407 436/127 |
| 2010/0217077 | A1 * | 8/2010 | Gono | A61B 1/0655 600/109 |
| 2011/0296538 | A1 * | 12/2011 | Segall | G01N 33/574 424/9.2 |
| 2012/0013722 | A1 * | 1/2012 | Wong | G01J 3/0224 348/66 |
| 2013/0006109 | A1 * | 1/2013 | Takei | A61B 1/0638 600/432 |
| 2014/0088358 | A1 * | 3/2014 | Banik | A61B 1/008 600/141 |
| 2014/0272764 | A1 * | 9/2014 | Miller | A61B 6/14 433/29 |
| 2015/0198600 | A1 * | 7/2015 | Nagele | G01N 33/57484 506/18 |
| 2015/0223675 | A1 * | 8/2015 | Sella-Tavor | A61B 5/4255 600/431 |
| 2015/0320320 | A1 * | 11/2015 | Kopelman | A61B 6/14 433/215 |
| 2016/0345802 | A1 * | 12/2016 | Nir | A61B 1/00045 |
| 2017/0079517 | A1 * | 3/2017 | Özcan | A61B 1/00034 |
| 2017/0340198 | A1 * | 11/2017 | Elazar | H05B 45/22 |
| 2019/0053709 | A1 * | 2/2019 | Chen | G06V 10/54 |
| 2020/0138265 | A1 * | 5/2020 | Endo | A61B 1/000094 |
| 2020/0169649 | A1 * | 5/2020 | Ouyang | A61B 1/00064 |
| 2020/0297266 | A1 * | 9/2020 | Perelman | A61B 5/0075 |
| 2021/0012495 | A1 * | 1/2021 | Kamon | G06T 7/0012 |
| 2021/0076917 | A1 * | 3/2021 | Kamon | A61B 1/045 |
| 2021/0127980 | A1 * | 5/2021 | Devaraju | A61B 5/0075 |
| 2021/0307597 | A1 * | 10/2021 | Wilder Smith | A61B 5/7275 |

* cited by examiner

M/F: Patient Gender

Y/N: age (40+), Family history of cancer, Employed, Regular Dentist Visit, Symptoms (oral lesion, lump in neck, difficulty opening mouth, mouth ulcer, white or red patch in mouth, swelling in neck, growth in mouth)

None, moderate, severe: Alcohol, Cigarette Smoker, Pipe Smoker, Cigar Smoker, Chewing Tobacco

If yes for mouth ulcer or sore: duration, number of lesions, pain, loss of sensation, everted surrounding tissue If yes for white patch: duration, color, number of lesions, can it be wiped off, regular/irregular surface, uniform surface, pain If yes for swelling in neck: duration, consistency, mobile/fixed, smooth/normal/rough skin over swelling, location, size, If yes for growth: duration, change in size, pain, loss of sensation, consistency, regular/irregular surface over growth, loose adjacent teeth

ORAL AND OROPHARYNGEAL CANCER SCREENING SYSTEM AND METHODS OF USE

RELATED APPLICATIONS

This application is a 35 U.S.C. § 371 US national stage entry and is entitled to the earliest effective filing date of international application number PCT/US2019/042811, filed on Jul. 22, 2019, which itself claims priority U.S. provisional application Ser. No. 62/702,184, filed on Jul. 23, 2018. The contents of the aforementioned applications are incorporated herein by reference.

GOVERNMENT LICENSE RIGHTS

This invention was made with Government support under Grant No. EB022623, awarded by the National Institutes of Health. The Government has certain rights in the invention.

BACKGROUND

The subject of this provisional patent application relates generally to oropharyngeal and dental instruments and devices, and more particularly to an oral and oropharyngeal cancer screening and monitoring system and associated methods of use.

Applicant(s) hereby incorporate herein by reference any and all patents and published patent applications cited or referred to in this application.

By way of background, more than two-thirds of oral and oropharyngeal cancers (hereinafter collectively "OC" for simplicity purposes) are typically detected after they have spread, resulting in a five-year survival rate of approximately twenty percent (20%). However, if detected early, five-year survival rates can be approximately eighty percent (80%). Current visual screening methods for OC or potentially premalignant lesions ("OPML") by non-specialists tend to have little diagnostic value, and no other non-specialist options are currently available. While screening is typically performed with the naked eye, adjuncts that may be used include intraoral cameras and various imaging approaches. Existing intraoral cameras, for example, are typically around 15-25 mm in diameter—i.e., the size of 2-3 teeth—with only an 80-90 degree viewing field, and a relatively rigid design. Such a design hinders access to many high-risk areas of the mouth, and considerably limits the camera's ability to image entire soft tissue lesions or screening sites. For example, the borders or base of the tongue, or the buccal mucosa are too large for single-image photographs. As a result, some cancers, including HPV-related cancers, may not be readily accessible for discovery by such existing intraoral cameras. Existing adjuncts based on auto-fluorescence, spectroscopy or other optical or other techniques are cumbersome to use, have poor access, poor specificity, no ability to store or compare data digitally or otherwise, show considerable user error/variability, and are not well-suited for non-specialist use, where detection screening and initial diagnosis typically occur. Additionally, specialists currently diagnose oral cancer by surgical biopsy, with the tissue samples then being sent to specialist labs for processing, sectioning, staining and diagnosis by a specialized oral pathologist. As a result, current specialist means tend to be slow, costly and have very limited accessibility. For individuals who have potentially premalignant lesions in the oral cavity (OPML), surveillance is currently the standard of care. Yet visual surveillance has very poor accuracy, and specialist surveillance typically involves repeated biopsies, leading to very poor recall compliance in these individuals, and late diagnosis of malignant change.

Thus, there remains a need for an effective, non-specialist system and associated methods for screening for, detecting, diagnosing and monitoring OC and OPML.

Aspects of the present invention fulfill these needs and provide further related advantages as described in the following summary.

It should be noted that the above background description includes information that may be useful in understanding aspects of the present invention. It is not an admission that any of the information provided herein is prior art or relevant to the presently claimed invention, or that any publication specifically or implicitly referenced is prior art.

SUMMARY

Aspects of the present invention teach certain benefits in construction and use which give rise to the exemplary advantages described below.

The present invention solves the problems described above by providing an oral and oropharyngeal cancer screening system and associated methods. In at least one embodiment, the screening system provides an at least one oral oropharyngeal cancer screening device configured for selectively capturing images of an oropharyngeal area of an at least one patient. The screening device provides an elongate, relatively compact housing, a distal end of the housing being selectively bendable. An imaging module is positioned within the housing, the imaging module providing a lens, an at least one light source, and an imaging sensor positioned in the distal end of the housing. A user application resides in memory on an at least one user device in selective communication with the at least one screening device. The user application is configured for receiving images captured by the at least one screening device, along with select OPML/OC risk factors, automatically analyzing the captured images and potential health-related risk factors, and generating a screening output for OC risk, as well as any changes in OC risk level from previous visits.

Other features and advantages of aspects of the present invention will become apparent from the following more detailed description, taken in conjunction with the accompanying drawings, which illustrate, by way of example, the principles of aspects of the invention.

BRIEF DESCRIPTION OF THE DRAWINGS

The accompanying drawings illustrate aspects of the present invention. In such drawings.

The above described drawing figures illustrate aspects of the invention in at least one of its exemplary embodiments, which are further defined in detail in the following description. Features, elements, and aspects of the invention that are referenced by the same numerals in different figures represent the same, equivalent, or similar features, elements, or aspects, in accordance with one or more embodiments.

DETAILED DESCRIPTION

Figure 1:
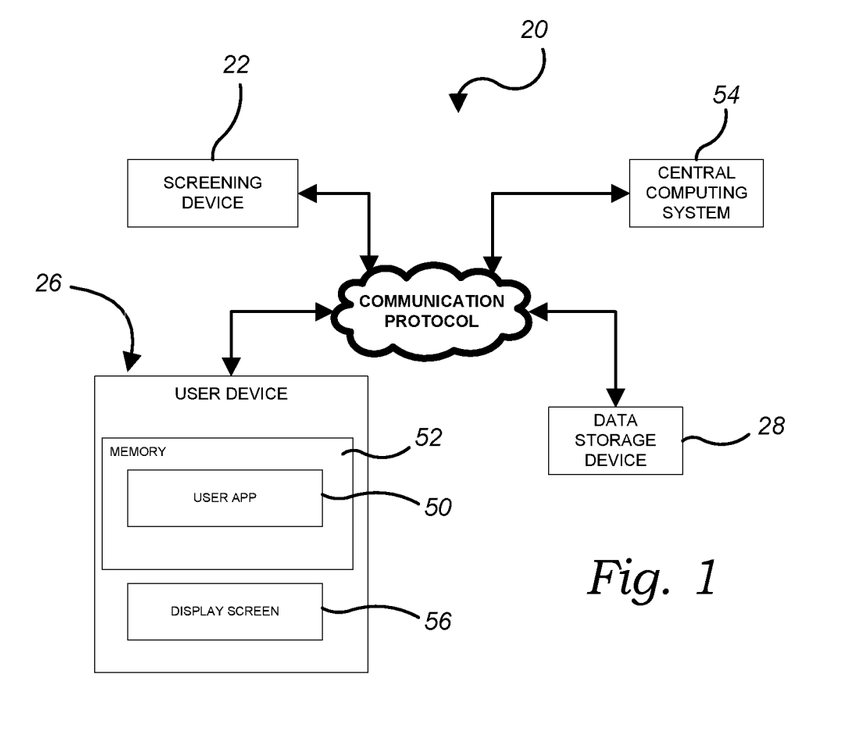
FIG. 1 is a simplified schematic view of an exemplary oral and oropharyngeal cancer screening system, in accordance with at least one embodiment.
Figure 2:
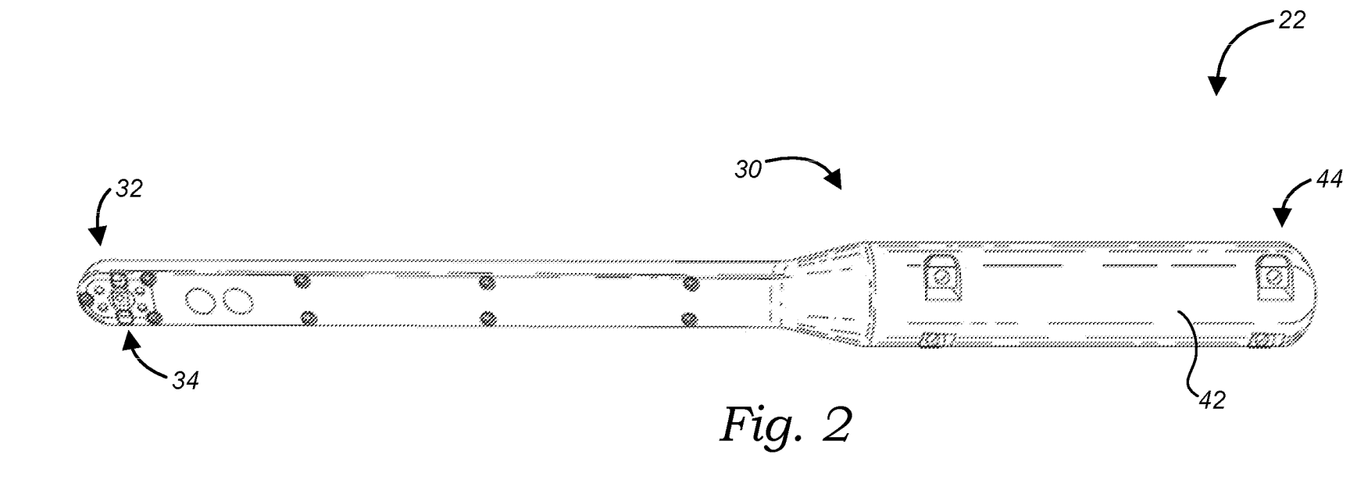
FIG. 2 is a perspective view of an exemplary screening device, in accordance with at least one embodiment.
Figure 3:
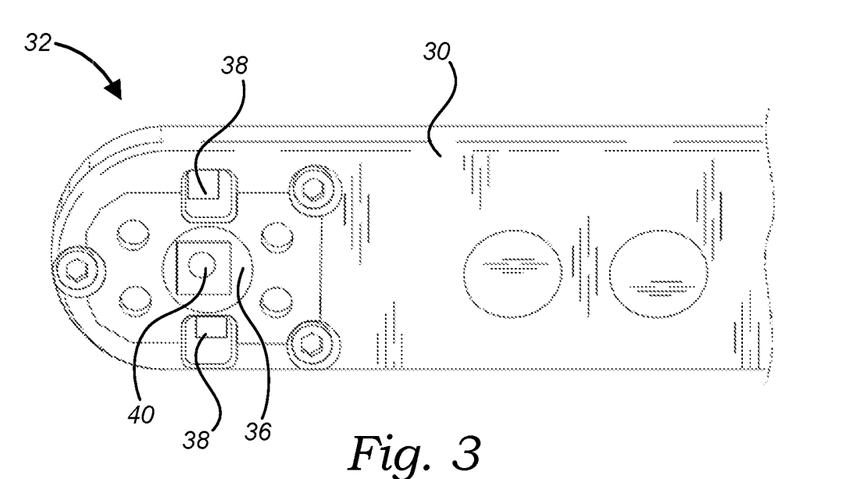
FIG. 3 is a further partial perspective view thereof.

Turning now to FIG. 1, there is shown a simplified schematic view of an exemplary oral and oropharyngeal cancer screening system 20 configured for screening for, detecting, diagnosing and monitoring OC and OPML. In at least one embodiment, the system 20 provides an oral and oropharyngeal cancer screening device 22 configured for selectively capturing images 24 (i.e., photos and/or video) of a patient's oropharyngeal area O, as discussed further below, and an at least one user device 26 in selective communication with the at least one screening device 22 and configured for receiving and processing data related to the patient's oropharyngeal area O, including the images 24 captured by the screening device 22 along with select OPML/OC risk factors, as discussed further below. In at least one embodiment, the user device 26 and the at least one screening device 22 are one and the same—as such, it is intended that those terms as used herein are to be interchangeable with one another. In at least one embodiment, the system 20 further provides an at least one data storage device 28 in selective communication with at least one of the at least one screening device 22 and at least one user device 26, and configured for storing said data related to the patient's oropharyngeal area O as obtained by the at least one screening device 22 and processed by the user device 26, along with certain other data as discussed further below. In at least one embodiment, the user device 22 and data storage device 28 are also one and the same—as such, it is intended that those terms as used herein are to be interchangeable with one another as well.

At the outset, it should be noted that communication between each of the at least one screening device 22, at least one user device 26, and at least one data storage device 28 may be achieved using any wired- or wireless-based communication protocol (or combination of protocols) now known or later developed. As such, the present invention should not be read as being limited to any one particular type of communication protocol, even though certain exemplary protocols may be mentioned herein for illustrative purposes. It should also be noted that the term "user device" is intended to include any type of computing or electronic device, now known or later developed, capable of substantially carrying out the functionality described herein—such as desktop computers, mobile phones, smartphones, laptop computers, tablet computers, personal data assistants, gaming devices, wearable devices, etc. As such, the screening system 20 should not be read as being limited to use with any one particular type of computing or electronic device, even though certain exemplary devices may be mentioned or shown herein for illustrative purposes. Additionally, in at least one embodiment, the at least one user device 26 is in the possession or control of at least one of the patient themselves, a clinician who is desirous of receiving the data related to the patient's oropharyngeal area O, or any other individual or entity (such as a parent or guardian, for example) who has an interest in receiving the data related to the patient's oropharyngeal area O, for which the patient has provided prior authorization to receive said data (collectively hereinafter referred to as "users" for simplicity purposes). In that regard, it should be noted that, in at least one embodiment, the term "clinician" is intended to generally include any type of medical professional or medical or public health, community-based worker or other interested entity. In at least one further embodiment, the at least one user device 26 is remotely accessible (such as through a server, for example) by the at least one patient, clinician, or any other individual or entity who has an interest in receiving the data.

Figure 4:
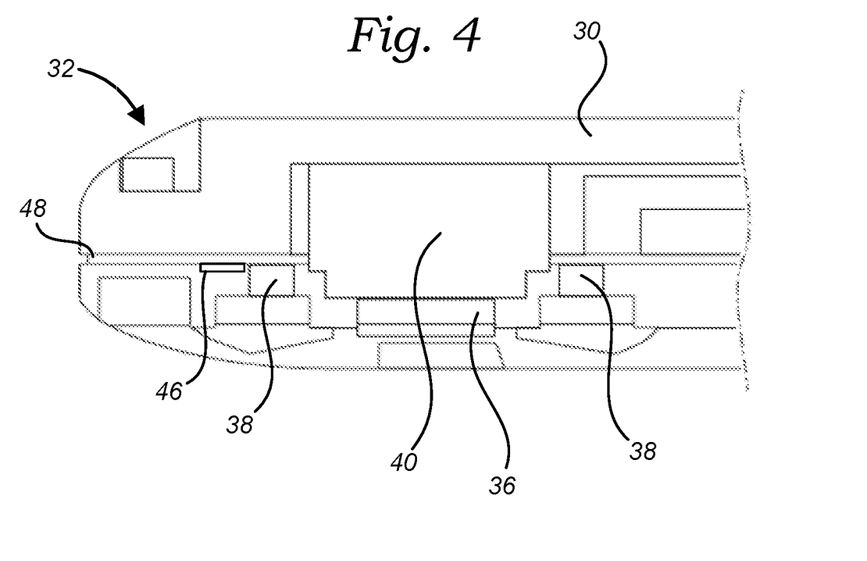
FIG. 4 is a partial diagrammatic view of the exemplary screening device, in accordance with at least one embodiment.
Figure 5:
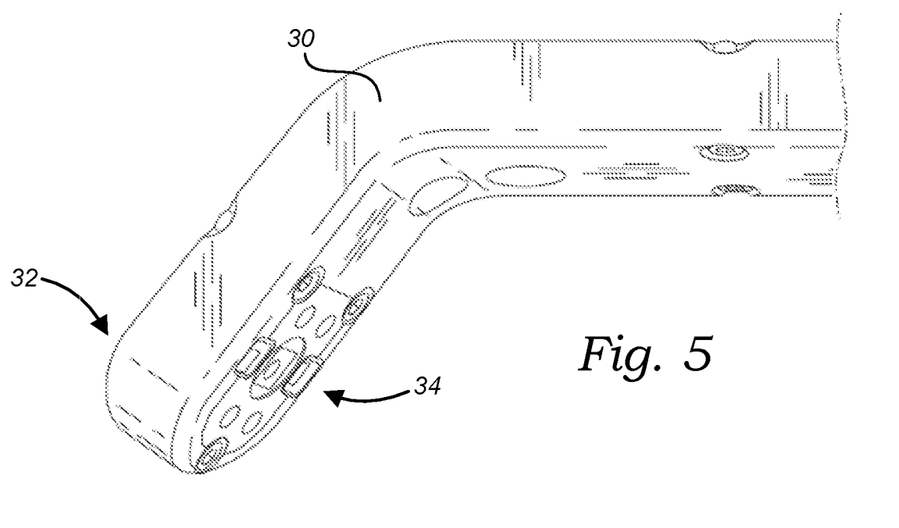
FIGS. 5 and 6 are further partial perspective views of the exemplary screening device, in accordance with at least one embodiment.
Figure 6:
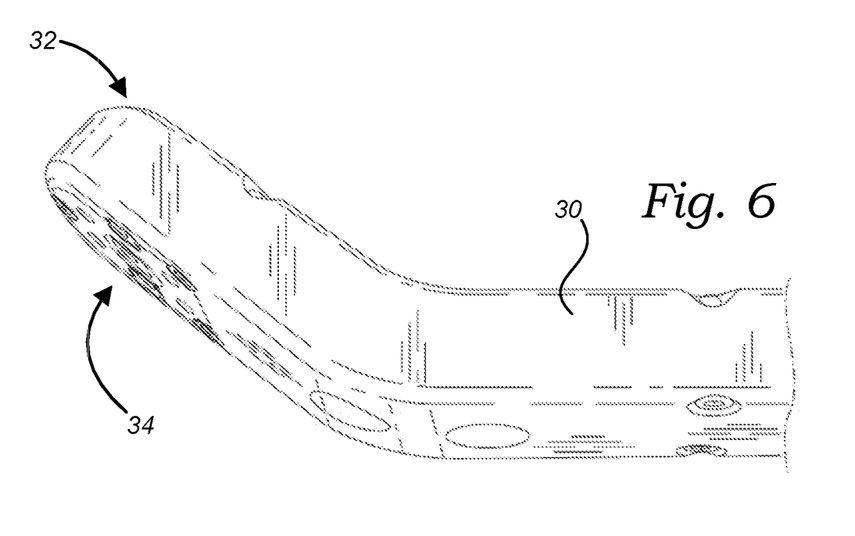

In at least one embodiment, as illustrated in FIGS. 2-6, the at least one screening device 22 has a relatively compact, aspherical, pen-shaped housing 30. In at least one such embodiment, a distal end 32 of the housing 30 has a diameter of approximately 10 mm, and a length of approximately 8 mm; though in further embodiments, the distal end 32 of the housing 30 may take on any other size, shape, or dimensions—now known or later developed—capable of allowing the screening device 22 to carry out the functionality described herein. In at least one embodiment, most of the external surfaces of the housing 30 are aspherical for better image quality and smaller size. In at least one embodiment, the distal end 32 of the housing 30 is selectively extendable. Additionally, in at least one embodiment, as illustrated in FIGS. 5 and 6, the distal end 32 of the housing 30 is selectively bendable, thereby allowing the screening device 22 to reach all areas of the patient's oropharyngeal area O. In at least one such embodiment, the distal end 32 is capable of bending up to 90 degrees; however, in further embodiments, the distal end 32 is capable of bending up to 360 degrees. In at least one embodiment, the housing 30 is made of a relatively soft medical-grade plastic. In at least one alternate embodiment, the housing 30 may be made of any other material, or combination of materials—now known or later developed—capable of allowing the screening device 22 to carry out the functionality described herein. Additionally, in at least one embodiment, an outer disposable sheath is engaged with the housing 30 for assisting with infection control.

In at least one embodiment, as illustrated in the partial diagrammatic view of FIG. 4, the housing 30 provides an imaging module 34 positioned and configured for capturing images 24 of the patient's oropharyngeal area O. In at least one embodiment, the imaging module 34 provides a lens 36, an at least one light source 38, and an imaging sensor 40. In at least one embodiment, the lens 36 is a fisheye lens configured for expanding the field of view to 120 degrees. In at least one such embodiment, the fisheye lens has a diameter of less than 5 mm and a distortion under five percent (5%). Additionally, in at least one embodiment, the imaging sensor 40 has an image area measuring 3.5 cm×3.5 cm. Thus, combined with the housing's 30 bendability, the screening device 22 is capable of capturing images 24 of all areas of the patient's oropharyngeal area O, in at least one embodiment, including posterior regions such as the base of the tongue and peritonsillar area. These high-risk sites for HPV-related OC cannot be examined in many patients using the naked eye or existing intraoral cameras or other adjunct devices.

In at least one embodiment, the imaging sensor 40 is a low-cost, high-performance 5-megapixel OV5648 imaging sensor with 2592×1944 pixels. However, in further embodiments, any other imaging sensor—now known or later developed—may be substituted, so long as the screening device 22 is capable of carrying out the functionality described herein. In at least one embodiment, to achieve greater flexibility of the distal end 32 of the housing 30, all electronics for the imaging sensor 40 and light source 38 are positioned inside a handle portion 42 of the screening device 22, at a proximal end 44 of the housing 30, with only the imaging sensor 40 itself, the imaging lens 36, and light source 38 positioned in the distal end 32 of the housing 30. In at least one embodiment, in order to remove specular reflection—which is a barrier to high quality images from existing intra-oral cameras—a polarizer is positioned in front of the light source 38 and an analyzer is used in front of the imaging lens 36. In at least one embodiment, the imaging sensor 40 is configured for capturing at least one of polarized white light images and autofluorescence images. Additionally, in at least one embodiment, a long-pass filter is positioned in front of the imaging sensor 40 to block the excitation light around 405 nm.

In at least one embodiment, the at least one light source 38 is an at least one LED; however, in further embodiments, the at least one light source 38 may comprise any other source of fluorescent and/or white light, now known or later developed. In at least one embodiment, where the at least one light source 38 is an at least one LED, the LED consists of a mounted, flexible printed circuit 46 ("FPC"), which is attached to one side of a flexible stainless steel strip 48. The imaging lens 36 and the imaging sensor 40 are each mounted on the other side of the stainless steel strip 48. In at least one embodiment, during use of the screening device 22 in an oral viewing mode, the LED provides constant illumination in a low power mode. Additionally, during use of the screening device 22 in an image capture mode, the LED automatically switches to a pulsed mode for better image quality.

As mentioned above, in at least one embodiment, the screening system 20 also provides an at least one user device 26 in selective communication with the at least one screening device 22 and configured for receiving and processing data related to the patient's oropharyngeal area O, including the images 24 captured by the screening device 22 along with select OPML/OC risk factors, as discussed further below. In at least one embodiment, each of the at least one screening device 22 and at least one user device 26 contains the hardware and software necessary to carry out the exemplary methods for screening for, detecting, diagnosing and monitoring OC and OPML, as described herein. Furthermore, in at least one embodiment, the user device 26 comprises a plurality of computing devices selectively working in concert with one another to carry out the exemplary methods described herein. In at least one embodiment, the user device 26 provides a user application 50 residing locally in memory 52 on the user device 26, the user application 50 being configured for selectively communicating with the at least one screening device 22, as discussed further below. In at least one alternate embodiment, the functionality provided by the user application 50 resides remotely in memory on a remote central computing system 54 (FIG. 1), with the at least one user device 26 capable of accessing said functionality via an online portal hosted by the computing system 54, either in addition to or in lieu of the user application 50 residing locally in memory 52 on the at least one user device 26. It should be noted that, for simplicity purposes, the functionality provided by the user application 50 will be described herein as such—even though certain embodiments may provide some or all of said functionality through an online portal. It should also be noted that, for simplicity purposes, when discussing functionality and the various methods that may be carried out by the screening system 20 herein, the terms "user device" and "user application" are intended to be interchangeable, in accordance with at least one embodiment. It should also be noted that the term "memory" is intended to include any type of electronic storage medium (or combination of storage mediums) now known or later developed, such as local hard drives, RAM, flash memory, secure digital ("SD") cards, external storage devices, network or cloud storage devices, integrated circuits, etc. In at least one embodiment, the user device 26 provides an at least one display screen 56 configured for displaying the data related to the patient's oropharyngeal area O, as discussed in detail below.

In at least one embodiment, the screening device 22 is configured for being selectively connected to the user device 26 via a wire, such as a USB cable for example. In at least one such embodiment, the screening device 22 is configured for being selectively powered by the user device 26, thereby eliminating the need for a local battery or other power source positioned within the screening device 22 itself. However, in at least one alternate embodiment, the screening device 22 provides a battery or other type of power source, now known or later developed. In at least one such alternate embodiment, the screening device 22 is in selective wireless communication with the at least one user device 26.

In use, in at least one embodiment, the system 20 is capable of screening for, detecting, diagnosing and monitoring OC and OPML. In at least one embodiment, images 24 and risk data captured by the screening device 22 are transmitted—either manually or automatically—to the user application 50, where they are processed. In at least one embodiment, image processing within the user application 50 will perform an adaptive image adjust for better image quality, and then utilize a deep learning image classification algorithm. In at least one embodiment, processing the captured images 24 includes automatically analyzing the captured images 24 and combining that data with information on potential health-related risk factors (such as for OC or OPML, for example). After processing the captured images 24, the user application 50 is configured for providing the user/patient with any pertinent information.

Figure 7:
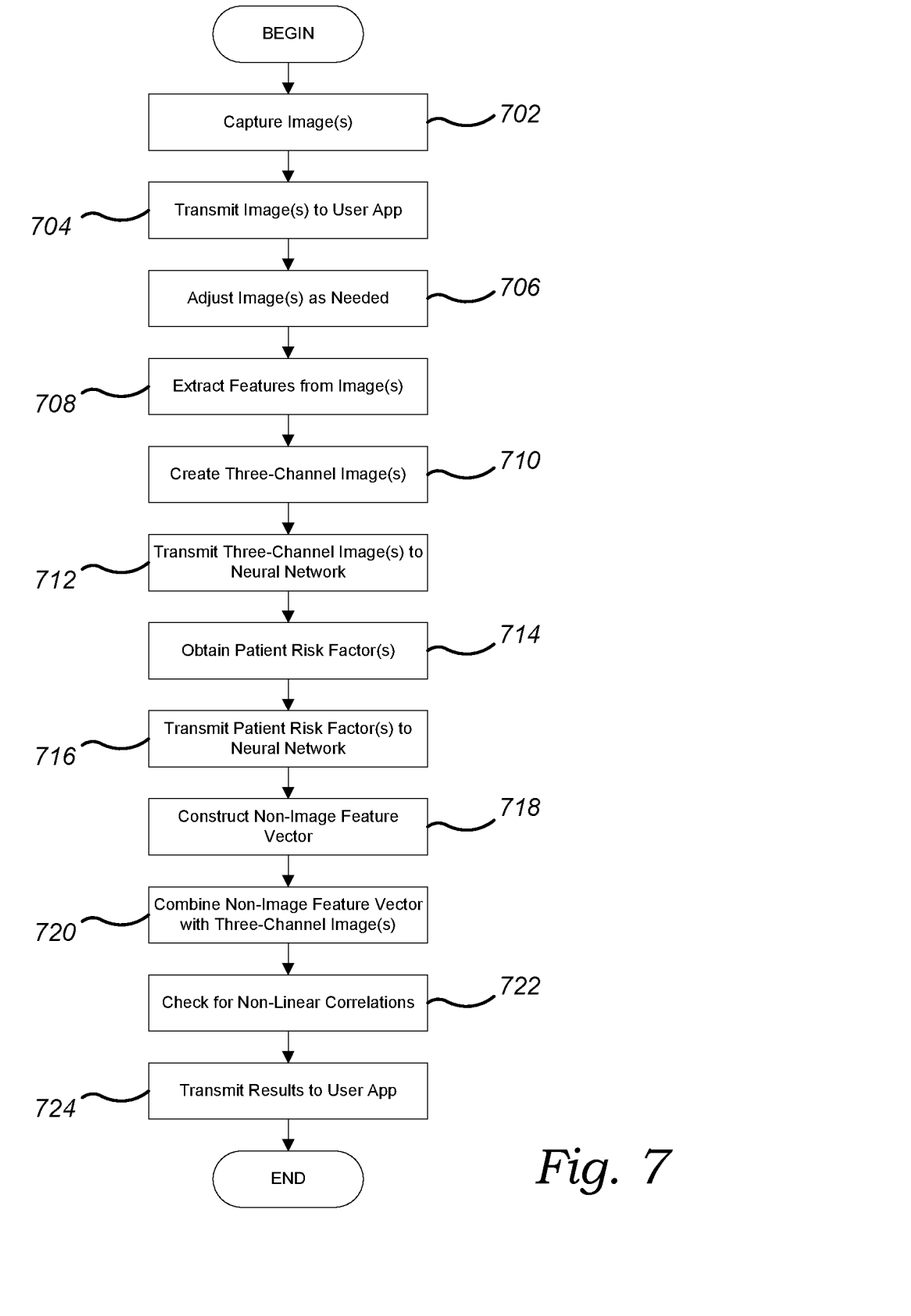
FIG. 7 is a flow diagram of an exemplary method for screening for, detecting, diagnosing and monitoring OC and OPML, in accordance with at least one embodiment.

In a bit more detail, in at least one embodiment, as illustrated in the flow diagram of FIG. 7, upon the imaging sensor 40 capturing one or more images 24 of a patient's oropharyngeal area O (702), the images 24 are transmitted to the user application 50 (704) so that the user application 50 may perform adaptive image adjustments for better image quality (706). In at least one such embodiment, upon the user application 50 detecting insufficient image quality for a given image 24, the user application 50 issues a notification to alert the user about the poor image quality, and prompting the user to obtain a new image 24 of the patient's oropharyngeal area(s) O. In at least one embodiment, for each image 24 that the user application 50 determines is of sufficient quality, color features—i.e., mean red to green brightness ratio, mean saturation, and mean brightness—as well as textural features—i.e., gray level co-occurrence matrix (GLCM), gray level run length matrix (GLRLM), and local binary patterns (LBP)—of each such image 24 are extracted (708). In at least one embodiment, the images 24 captured by the imaging sensor 40 are white light images. In at least one alternate embodiment, the images 24 captured by the imaging sensor 40 are autofluorescence images. In at least one still further embodiment, the images 24 captured by the imaging sensor 40 are a combination of white light images and autofluorescence images. In at least one such embodiment, where the imaging sensor 40 utilizes a long-pass filter to block the excitation light around 405 nm, the user application 50 is able to exclude a blue light channel from the white light images, leaving only red and green light channels. The user application 50 utilizes a sequential feature-selection method to compose a feature subset with the best classification performance. In at least one embodiment, where the imaging sensor 40 captures both a white light image and an autofluorescence image for a given image 24, the user application 50 creates a single three-channel image (710) by using the green and red channels individually from the associated white light image as the first and second channels, respectively, and the normalized ratio of red and green channels from the associated autofluorescence image as the third channel. Each of these three-channel images are then transmitted by the user application 50 to a neural network (executing either locally on the user device 26 or remotely on the central computing system 54) for evaluation (712), as discussed further below. In at least one embodiment, the neural network utilizes one of a VGG-CNN-M, VGG-CNN-S, and VGG-16 architecture. In at least one alternate embodiment, the neural network utilizes a convolutional architecture, such as Mobile-Net, SqueezeNet, AlexNet, or ShuffleNet, for example. In still further embodiments, the neural network may utilize any other architectures or techniques (or combinations thereof), now known or later developed, so long as the system 20 is substantially capable of carrying out the functionality described herein.

Figure 8:
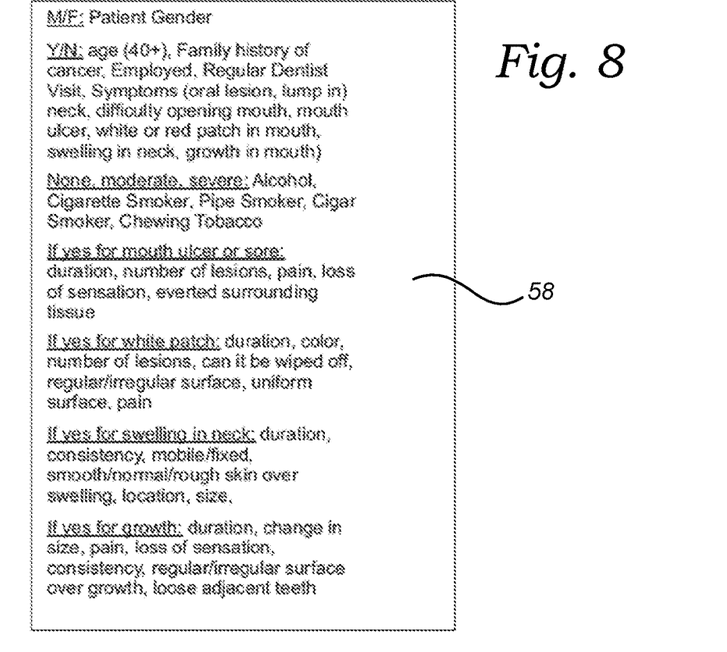
FIGS. 8 and 9 are illustrations of exemplary user interfaces as displayed by an exemplary user device, in accordance with at least one embodiment.

With continued reference to FIG. 7, in at least one embodiment, the user application 50 obtains select risk factors for OC in connection with the patient (714), which are then transmitted to the neural network (716) for evaluation in combination with the at least one three-channel image, in order to screen for, detect, diagnose and monitor OC and OPML. In at least one such embodiment, adding such risk behavior information to screening can considerably improve the system's 20 accuracy of OC risk assessment. In at least one embodiment, one or more of the risk factors are input into the user application 50 manually by the user. In at least one embodiment, one or more of the risk factors are obtained by the user application 50 automatically. FIG. 8 illustrates an exemplary user interface 58 providing exemplary risk factors. Further examples of risk factors (in the form of a checklist for illustrative purposes) include:

| | |
|---|---|
| Patient Gender: | Male |
| | Female |
| Age (40+): | Yes |
| | No |
| Family history of cancer: | Yes |
| | No |
| Education Level: | None |
| | High school |
| | College |
| Employed: | Yes |
| | No |
| Alcohol: | No |
| | Social |
| | Heavy |
| Smoker: | No |
| | Social |
| | Cigarette |
| | Pipe |
| | Cigar |
| | Other |
| Chewing Tobacco: | No |
| | Light |
| | Heavy |
| Visit Dentist: | Yes |
| | No |
| Any symptoms of: | Oral lesion |
| | Lump in neck |
| | Difficulty opening mouth |
| | Mouth ulcer |
| | White or red patch in mouth |
| | Swelling in neck |
| | Growth in mouth |
| If yes for mouth ulcer or sore: | Less than 3 weeks |
| | More than 3 weeks |
| | One ulcer |
| | Multiple ulcers |
| | Painful |
| | No pain |
| | Loss of sensation |
| | Reverted surrounding tissue |
| | Not reverted surrounding tissue |
| If yes for white patch: | Less than 3 weeks |
| | More than 3 weeks |
| | White colored patch |
| | White-red colored patch |
| | One white patch |
| | Multiple white patches |
| | Can be whipped off |
| | Cannot be whipped off |
| | Irregular patch surface |
| | Uniform patch surface |
| | Painful |
| | No pain |
| If yes for swelling in neck: | Less than 3 weeks |
| | More than 3 weeks |
| | Firm consistency |
| | Soft consistency |
| | Mobile swelling |
| | Fixed swelling |
| | Smooth skin over swelling |
| | Normal skin over swelling |
| | Irregular skin over swelling |
| | Lateral location in neck |
| | Midline location in neck |
| | Less than 2 centimeters in size |
| | 2-4 centimeters in size |
| | 4-6 centimeters in size |
| | More than 6 centimeters in size |
| If yes for growth: | Less than 3 weeks |
| | More than 3 weeks |
| | Increase in size |
| | No change in size |
| | Decrease in sized |
| | Painful |
| | Loss of sensation |
| | No pain |
| | Firm consistency |
| | Soft consistency |
| | Irregular surface overlying mucosa |
| | Regular surface overlying mucosa |
| | Loose teeth around growth |
| | Normal teeth around growth |

With continued reference to FIG. 7, in at least one embodiment, the neural network constructs a non-image feature vector using the risk factors provided by the user application 50 (718). The neural network then joins the non-image feature vector with the at least one three-channel image (720) in order to determine the existence of any non-linear correlations therebetween (722). In at least one embodiment, since the at least one three-channel image has a relatively higher dimension than the non-image feature vector, the neural network adds a further fully connected layer with N units (having the same the dimension as the non-image feature vector) to reduce the dimension of the convolutional neural network feature to be comparable with the non-image data. The N-dimension image feature and the N-dimension non-image feature are then concatenated together. In at least one embodiment, to automatically locate and segment the lesion area from its background, the user application 50 uses a MobileNet-SSD to perform rapid oral lesion localization on the user device 26. The single shot multibox detector ("SSD") uses a convolutional network as a base network that produces a fixed-size collection of bounding boxes and scores for the presence of object class instances in those boxes, and a non-maximum suppression step to produce the final detections.

Figure 9:
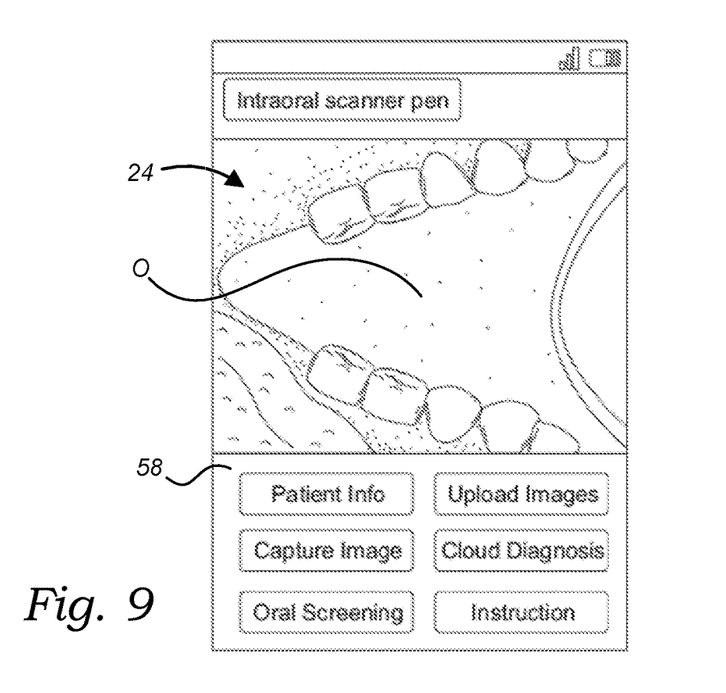

In at least one embodiment, as illustrated in the exemplary user interface of FIG. 9, the user application 50 provides various interactive functions to: (1) record expanded patient risk factor assessment as a simple Y/N checklist, for example (though other forms of assessment, now known or later developed, maybe substituted); (2) inspect the oropharyngeal area O; (3) capture images 24; (4) upload images 24 and risk assessment tabulation to the central computing system 54 and/or data storage device 28; and (5) receive triage guidance on OC risk and management from the neural network. In at least one embodiment, captured images 24 and risk assessment tabulation can be automatically or manually uploaded by the user with a single "click of a button" and, after the data is processed by the neural network, two sets of categorical information will be sent back to the user application 50 (724): (1) OC risk categorization (0: no risk; 1: low risk; and 2: high risk, or healthy, OPML, OC with potentially various breakdowns in severity of each main category) and (2) management guidance (no action; monitor; refer immediately). In at least one embodiment, comparison between captured images 24 is also possible for monitoring purposes, with feedback from the user application 50 being (1) OC risk change (no change; somewhat increased risk; greatly increased risk) and (2) management guidance (no action; monitor; refer immediately). In at least one further embodiment, the screening system 20 is capable of creating a bounding box around a region of interest within the patient's oropharyngeal area O (via the image 24 on the display screen 56), and this information could be sent back to the user giving them the opportunity to take a second image 24 more focused on the region of interest. This can be very useful clinically, as visual inspection performs very poorly in identifying and mapping areas of increased risk that require further examination or biopsy.

Thus, in at least one embodiment, the screening system 20 is capable of automatically detecting, mapping, monitoring, and diagnosing oral tissues, vasculature and other targets at all sites of the mouth for health and/or pathology—all in a way that is ideal for non-specialist or clinical use in non-specialist or clinical settings; will improve screening accuracy to ensure earlier and more accurate entry to the path of care for OPML and OC; far quicker and less expensive than specialist services; relatively low risk (as compared to the risks associated with biopsies); relatively faster with immediate clinical decision-making guidance; non-invasive; and capable of linking directly with existing wireless and smartphone technologies for data transfer/sharing, cloud-based algorithm access, remote specialist access, telemedicine, telehealth and teledentistry, and longitudinal lesion monitoring.

Aspects of the present specification may also be described as the following embodiments:

1. An oral and oropharyngeal cancer screening device configured for selectively capturing images of an oropharyngeal area of an at least one patient, the device comprising: an elongate, relatively compact housing, a distal end of the housing being selectively bendable; and an imaging module positioned within the housing, the imaging module providing a lens, an at least one light source, and an imaging sensor positioned in the distal end of the housing.

2. The screening device according to embodiment 1, wherein the housing is relatively aspherical.

3. The screening device according to embodiments 1-2, wherein the distal end of the housing has a diameter of approximately 10 mm.

4. The screening device according to embodiments 1-3, wherein the distal end of the housing has a length of approximately 8 mm.

5. The screening device according to embodiments 1-4, wherein the distal end of the housing is selectively extendable.

6. The screening device according to embodiments 1-5, wherein the distal end of the housing is capable of bending up to 90 degrees.

7. The screening device according to embodiments 1-6, wherein the lens is a fisheye lens configured for expanding a field of view of the imaging module to 120 degrees.

8. The screening device according to embodiments 1-7, wherein the fisheye lens has a diameter of less than 5 mm and a distortion under five percent (5%).

9. The screening device according to embodiments 1-8, wherein the imaging sensor has an image area measuring 3.5 cm×3.5 cm.

10. The screening device according to embodiments 1-9, wherein the imaging sensor is configured for capturing at least one of polarized white light images and autofluorescence images.

11. The screening device according to embodiments 1-10, wherein the imaging module further provides a long-pass filter positioned in front of the imaging sensor to block excitation light.

12. The screening device according to embodiments 1-11, further comprising: a polarizer positioned in front of the light source; and an analyzer positioned in front of the lens; whereby, the polarizer and analyzer are configured for removing any specular reflection.

13. The screening device according to embodiments 1-12, wherein the at least one light source is an at least one LED.

14. The screening device according to embodiments 1-13, wherein: the LED consists of a mounted, flexible printed circuit, which is attached to one side of a flexible stainless steel strip; and each of the lens and the imaging sensor is mounted on an opposing side of the stainless steel strip.

15. The screening device according to embodiments 1-14, wherein: during use of the screening device in an oral viewing mode, the LED provides constant illumination in a low power mode; and during use of the screening device in an image capture mode, the LED automatically switches to a pulsed mode for better image quality.

16. An oral and oropharyngeal cancer screening system comprising: an at least one oral and oropharyngeal cancer screening device configured for selectively capturing images of an oropharyngeal area of an at least one patient, the device comprising: an elongate, relatively compact housing, a distal end of the housing being selectively bendable; and an imaging module positioned within the housing, the imaging module providing a lens, an at least one light source, and an imaging sensor positioned in the distal end of the housing; and a user application residing in memory on an at least one user device in selective communication with the at least one screening device, the user application configured for: receiving images captured by the at least one screening device; recording information on oral and oropharyngeal cancer as well as OPML risk factors; and automatically analyzing the captured images and potential health-risk factors to screen for OPML and oral and oropharyngeal risk status and changes in that status.

17. The screening system according to embodiment 16, further comprising an at least one data storage device in selective communication with at least one of the at least one screening device and at least one user device, and configured for storing data related to the oropharyngeal area of the at least one patient.

18. The screening system according to embodiments 16-17, wherein the housing of the at least one screening device is relatively aspherical.

19. The screening system according to embodiments 16-18, wherein the distal end of the housing has a diameter of approximately 10 mm.

20. The screening system according to embodiments 16-19, wherein the distal end of the housing has a length of approximately 8 mm.

21. The screening system according to embodiments 16-20, wherein the distal end of the housing is selectively extendable.

22. The screening system according to embodiments 16-21, wherein the distal end of the housing is capable of bending up to 90 degrees.

23. The screening system according to embodiments 16-22, wherein the lens of the at least one screening device is a fisheye lens configured for expanding a field of view of the imaging module to 120 degrees.

24. The screening system according to embodiments 16-23, wherein the fisheye lens has a diameter of less than 5 mm and a distortion under five percent (5%).

25. The screening system according to embodiments 16-24, wherein the imaging sensor of the at least one screening device has an image area measuring 3.5 cm×3.5 cm.

26. The screening system according to embodiments 16-25, wherein the imaging sensor is configured for capturing at least one of polarized white light images and autofluorescence images.

27. The screening system according to embodiments 16-26, wherein the imaging module further provides a long-pass filter positioned in front of the imaging sensor to block excitation light.

28. The screening system according to embodiments 16-27, further comprising: a polarizer positioned in front of the light source of the at least one screening device; and an analyzer positioned in front of the lens of the at least one screening device; whereby, the polarizer and analyzer are configured for removing any specular reflection.

29. The screening system according to embodiments 16-28, wherein the at least one light source is an at least one LED.

30. The screening system according to embodiments 16-29, wherein: the LED consists of a mounted, flexible printed circuit, which is attached to one side of a flexible stainless steel strip; and each of the lens and the imaging sensor is mounted on an opposing side of the stainless steel strip.

31. The screening system according to embodiments 16-30, wherein: during use of the at least one screening device in an oral viewing mode, the LED provides constant illumination in a low power mode; and during use of the at least one screening device in an image capture mode, the LED automatically switches to a pulsed mode for better image quality.

32. A method for identifying oral and oropharyngeal cancer within an oropharyngeal area of a patient using the screening system according to embodiments 16-31, the method comprising the steps of: the imaging sensor capturing an at least one image of the oropharyngeal area; the screening device transmitting the at least one image to the user application; the user application extracting an at least one color feature and an at least one textural feature from each of the at least one image; the user application obtaining an at least one risk factor associated with the patient; the user application transmitting the at least one color feature, the at least one textural feature, and the at least one risk factor to a neural network; and the neural network analyzing each of the at least one color feature, at least one textural feature, and at least one risk factor to determine the presence of oral or oropharyngeal cancer.

33. The method according to embodiment 32, further comprising the step of the user application performing select adjustments to the at least one image so as to increase the quality of the at least one image.

34. The method according to embodiments 32-33, wherein the step of the user application extracting an at least one color feature and an at least one textural feature from each of the at least one image further comprises the step of the user application extracting at least one of a mean red to green brightness ratio, a mean saturation, a mean brightness, a gray level co-occurrence matrix, a gray level run length matrix, and a local binary pattern.

35. The method according to embodiments 32-34, wherein the step of the imaging sensor capturing an at least one image of the oropharyngeal area further comprises the step of the imaging sensor capturing at least one of a white light image and an autofluorescence image of the oropharyngeal area.

36. The method according to embodiments 32-35, wherein the step of the imaging sensor capturing an at least one image of the oropharyngeal area further comprises the step of the imaging sensor capturing each of a white light image and an autofluorescence image of the oropharyngeal area.

37. The method according to embodiments 32-36, further comprising the step of the user application creating a single three-channel image by using a green channel and a red channel individually from the associated white light image as the first and second channels, respectively, and a normalized ratio of red and green channels from the associated autofluorescence image as the third channel.

38. The method according to embodiments 32-37, further comprising the step of the neural network constructing a non-image feature vector using the at least one risk factor provided by the user application.

39. The method according to embodiments 32-38, further comprising the step of the neural network joining the non-image feature vector with the at least one three-channel image in order to determine the existence of any non-linear correlations therebetween.

40. The method according to embodiments 32-39, further comprising the steps of: the neural network increasing the size of the at least one three-channel image to have the same dimensions as the non-image feature vector, thereby forming an image feature vector; and the neural network concatenating the image feature vector and the non-image feature vector.

In closing, regarding the exemplary embodiments of the present invention as shown and described herein, it will be appreciated that an oral and oropharyngeal cancer screening system and associated methods are disclosed for screening for, detecting, diagnosing and monitoring OC and OPML. Because the principles of the invention may be practiced in a number of configurations beyond those shown and described, it is to be understood that the invention is not in any way limited by the exemplary embodiments, but is generally directed to an oral and oropharyngeal cancer screening system and is able to take numerous forms to do so without departing from the spirit and scope of the invention. It will also be appreciated by those skilled in the art that the present invention is not limited to the particular geometries and materials of construction disclosed, but may instead entail other functionally comparable structures or materials, now known or later developed, without departing from the spirit and scope of the invention.

Certain embodiments of the present invention are described herein, including the best mode known to the inventor(s) for carrying out the invention. Of course, variations on these described embodiments will become apparent to those of ordinary skill in the art upon reading the foregoing description. The inventor(s) expect skilled artisans to employ such variations as appropriate, and the inventor(s) intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein. Similarly, as used herein, unless indicated to the contrary, the term "substantially" is a term of degree intended to indicate an approximation of the characteristic, item, quantity, parameter, property, or term so qualified, encompassing a range that can be understood and construed by those of ordinary skill in the art.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (along with equivalent open-ended transitional phrases thereof such as "including," "containing" and "having") encompasses all the expressly recited elements, limitations, steps and/or features alone or in combination with un-recited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amendment for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones.

The meaning of the closed-ended transitional phrase "consisting of" is being defined as only including those elements, limitations, steps and/or features specifically recited in the claim, whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (along with equivalent open-ended transitional phrases thereof) includes within its meaning, as a limiting case, claimed subject matter specified by the closed-ended transitional phrases "consisting of" or "consisting essentially of." As such, embodiments described herein or so claimed with the phrase "comprising" are expressly or inherently unambiguously described, enabled and supported herein for the phrases "consisting essentially of" and "consisting of."

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

It should be understood that the logic code, programs, modules, processes, methods, and the order in which the respective elements of each method are performed are purely exemplary. Depending on the implementation, they may be performed in any order or in parallel, unless indicated otherwise in the present disclosure. Further, the logic code is not related, or limited to any particular programming language, and may comprise one or more modules that execute on one or more processors in a distributed, non-distributed, or multiprocessing environment.

While aspects of the invention have been described with reference to at least one exemplary embodiment, it is to be clearly understood by those skilled in the art that the invention is not limited thereto. Rather, the scope of the invention is to be interpreted only in conjunction with the appended claims and it is made clear, here, that the inventor(s) believe that the claimed subject matter is the invention.

What is claimed is:

1. An oral and oropharyngeal cancer screening device configured for selectively capturing images of an oropharyngeal area of an at least one patient, the device comprising:
   an elongate, relatively compact housing;
   a proximal end of the housing providing a rigid handle portion;
   a distal end of the housing providing an elongate, rigid shaft portion engaged with a terminal end of the handle portion and extending there from in a direction substantially parallel with a longitudinal axis of the handle portion, the shaft portion having a diameter that is relatively smaller than a diameter of the handle portion;
   a terminal end of the shaft portion providing a substantially planar imaging surface oriented substantially parallel with a longitudinal axis of the shaft portion, the terminal end of the shaft portion being selectively pivotable relative to the longitudinal axis of the shaft portion, such that the terminal end of the shaft portion is capable of pivoting in each of a first direction and an opposing second direction relative to the longitudinal axis of the rigid shaft portion; and
   an imaging module positioned on the imaging surface of the terminal end of the shaft portion, the imaging module providing a fisheye lens, an at least one light source, and an imaging sensor, wherein an optical axis of the fisheye lens is oriented substantially normal to the longitudinal axis of the shaft portion.

2. The screening device of claim 1, wherein the housing is relatively aspherical.

3. The screening device of claim 1, wherein the terminal end of the shaft portion has a diameter of approximately 10 mm.

4. The screening device of claim 3, wherein the terminal end of the shaft portion has a length of approximately 8 mm.

5. The screening device of claim 1, wherein the shaft portion is selectively extendable.

6. The screening device of claim 1, wherein the terminal end of the shaft portion is capable of pivoting up to 90 degrees relative to the longitudinal axis of the rigid shaft portion.

7. The screening device of claim 1, wherein the fisheye lens is configured for expanding a field of view of the imaging module to 120 degrees.

8. The screening device of claim 1, wherein the imaging sensor is configured for capturing at least one of polarized white light images and autofluorescence images.

9. The screening device of claim 8, wherein the imaging module further provides a long-pass filter positioned in front of the imaging sensor to block excitation light.

10. The screening device of claim 1, further comprising:
    a polarizer positioned in front of the light source; and
    an analyzer positioned in front of the fisheye lens;
    whereby, the polarizer and analyzer are configured for removing any specular reflection.

11. An oral and oropharyngeal cancer screening system comprising:
    an at least one oral and oropharyngeal cancer screening device configured for selectively capturing images of an oropharyngeal area of an at least one patient, the device comprising:
    an elongate, relatively compact housing;
    a proximal end of the housing providing a rigid handle portion;
    a distal end of the housing providing an elongate, rigid shaft portion engaged with a terminal end of the handle portion and extending therefrom in a direction substantially parallel with a longitudinal axis of the handle portion, the shaft portion having a diameter that is relatively smaller than a diameter of the handle portion;
    a terminal end of the shaft portion providing a substantially planar imaging surface oriented substantially parallel with a longitudinal axis of the shaft portion, the terminal end of the shaft portion being selectively pivotable relative to the longitudinal axis of the shaft portion, such that the terminal end of the shaft portion is capable of pivoting in each of a first direction and an opposing second direction relative to the longitudinal axis of the rigid shaft portion; and an imaging module positioned on the imaging surface of the terminal end of the shaft portion, the imaging module providing a fisheye lens, an at least one light source, and an imaging sensor, wherein an optical axis of the fisheye lens is oriented substantially normal to the longitudinal axis of the shaft portion; and a user application residing in memory on an at least one user device in selective communication with the at least one screening device, the user application configured for, using an at least one hardware processor in communication with the memory:

receiving images of the oropharyngeal area of the at least one patient as captured by the at least one screening device;

obtaining an at least one risk factor associated with the at least one patient; and automatically analyzing the captured images and at least one risk factor to screen for oral and oropharyngeal cancer risk status and changes in that status.

12. The screening system of claim 11, further comprising an at least one data storage device in selective communication with at least one of the at least one screening device and at least one user device, and configured for storing data related to the oropharyngeal area of the at least one patient.

13. A method for identifying oral and oropharyngeal cancer within an oropharyngeal area of a patient using the screening system of claim 11, the method comprising the steps of:

the imaging sensor capturing each of a white light image and an autofluorescence image of the oropharyngeal area;

the screening device transmitting the white light image and autofluorescence image to the user application;

the user application creating an at least one three-channel image by using a green channel and a red channel individually from the associated white light image as the first and second channels, respectively, and a normalized ratio of red and green channels from the associated autofluorescence image as the third channel;

the user application extracting an at least one color feature and an at least one textural feature from each of the at least one three-channel image;

the user application obtaining an at least one risk factor associated with the patient;

the user application transmitting the at least one color feature, the at least one textural feature, and the at least one risk factor to a neural network;

the neural network constructing a non-image feature vector using the at least one risk factor provided by the user application;

the neural network concatenating the non-image feature vector with the at least one three-channel image in order to determine the existence of any non-linear correlations therebetween;

the neural network analyzing each of the at least one color feature, at least one textural feature, and at least one risk factor to determine the presence of oral or oropharyngeal cancer.

14. The method of claim 13, wherein the step of the user application extracting an at least one color feature and an at least one textural feature from each of the at least one image further comprises the step of the user application extracting at least one of a mean red to green brightness ratio, a mean saturation, a mean brightness, a gray level co-occurrence matrix, a gray level run length matrix, and a local binary pattern.

15. The method of claim 13, wherein the step of the imaging sensor capturing an at least one image of the oropharyngeal area further comprises the step of the imaging sensor capturing at least one of a white light image and an autofluorescence image of the oropharyngeal area.

16. The method of claim 13, further comprising the steps of:

the neural network increasing the size of the at least one three-channel image to have the same dimensions as the non-image feature vector, thereby forming an image feature vector; and the neural network concatenating the image feature vector and the non-image feature vector.

* * * * *